United States Patent
Raif et al.

(10) Patent No.: US 7,690,382 B2
(45) Date of Patent: Apr. 6, 2010

(54) SYSTEM AND METHOD FOR SALIVARY STONES REMOVAL AND JOINT ARTHROSCOPY

(75) Inventors: Joshua Raif, Kiryat Ono (IL); Oded Nahlieli, Ashkelon (IL); Michael Ariel Vardi, Herzeliya (IL)

(73) Assignee: Sialo-Lite, Ltd., Asheklon (IL)

( * ) Notice: Subject to any disclaimer, the term of this patent is extended or adjusted under 35 U.S.C. 154(b) by 647 days.

(21) Appl. No.: 11/180,917

(22) Filed: Jul. 14, 2005

(65) Prior Publication Data

US 2006/0084958 A1 Apr. 20, 2006

Related U.S. Application Data

(63) Continuation-in-part of application No. 10/762,583, filed on Jan. 23, 2004.

(30) Foreign Application Priority Data

Jan. 24, 2003 (IL) .................................. 154120

(51) Int. Cl.
*A61B 19/00* (2006.01)
(52) U.S. Cl. ..................... 128/898; 606/15; 607/88
(58) Field of Classification Search ............ 606/2–16; 607/88, 89; 600/101; 128/898
See application file for complete search history.

(56) References Cited

U.S. PATENT DOCUMENTS

| | | | | |
|---|---|---|---|---|
| 4,917,083 A | * | 4/1990 | Harrington et al. ............ 606/15 |
| 4,930,504 A | * | 6/1990 | Diamantopoulos et al. ..... 607/88 |
| 5,147,354 A | * | 9/1992 | Boutacoff et al. ............. 606/15 |
| 5,304,167 A | * | 4/1994 | Freiberg ........................ 606/3 |
| 5,363,387 A | | 11/1994 | Sinofsky |
| 5,374,266 A | | 12/1994 | Kataoka et al. |
| 5,458,594 A | | 10/1995 | Mueller et al. |
| 5,582,190 A | | 12/1996 | Slavin et al. |
| 5,693,043 A | * | 12/1997 | Kittrell et al. ................. 606/15 |
| 5,951,543 A | * | 9/1999 | Brauer .......................... 606/10 |
| 5,971,755 A | | 10/1999 | Liebermann et al. |
| 6,129,721 A | | 10/2000 | Kataoka et al. |
| 6,375,651 B2 | | 4/2002 | Grasso, III et al. |
| 6,395,000 B1 | | 5/2002 | Mitchell et al. |
| 6,450,170 B1 | | 9/2002 | Friedman |
| 6,709,269 B1 | * | 3/2004 | Altshuler ...................... 433/29 |

OTHER PUBLICATIONS

ADKiT "Journal of Otolaryngology, Endoscopic Laser Lithotripsy of a Proximal Parotid Duct Calculus," 3 Pages. Apr. 30, 2001.*
Teichman et a. "Journal of Urology, Erbium: Yag Versus Holmium: Yag Lithotripsy," vol. 165, pp. 876-879 (2001).*

(Continued)

*Primary Examiner*—Ahmed M Farah
(74) *Attorney, Agent, or Firm*—Browdy & Neimark, PLLC (57) ABSTRACT

A method and probe device are presented, suitable for use in joint arthroscopy. A beam of pulsed laser radiation of a wavelength range of about 2700-3000 nm and a predetermined frequency of pulses is produced, directed to a joint region inside a fluid medium and maintained substantially focused on a treatment target within the joint region during a predetermined time period. By this, a tissue within the treatment target is effected by the laser radiation.

8 Claims, 4 Drawing Sheets

OTHER PUBLICATIONS

Chang et al "Erbium: Yag Laser Lithotripsy Mechanism" Journal of Urology, (Aug. 2002) vol. 168, pp. 436-441.
Teichman et al "Erbium: Yag Versus Holmium: Yag Lithotripsy" Journal of Urology, (Mar. 2001) vol. 165, pp. 876-879.
Journal of Otolaryngology, Apr. 30, 2001, "Endoscopic Laser Lithotripsy of a Proximal Parotid Duct Calculus" 3 pages.
H. Ito et al., "Pulsed dye laser lithotripsy of submandibular gland salivary calculus," J. Laryngol Otol Oct. 1996; 110 (10):942-6.
E. Arzoz et al., "Endoscopic intracorporeal lithotripsy for sialolithiasis", J Oral Maxillofac Surg Jul. 1996; 54(7):847-50.
D. W. Chu et al., "Endoscopic management of submandibular sialolithiasis", Surg Endosc (2003) 17:876-879.

* cited by examiner

SYSTEM AND METHOD FOR SALIVARY STONES REMOVAL AND JOINT ARTHROSCOPY

CROSS REFERENCE TO RELATED APPLICATIONS

The present application is a continuation-in-part of U.S. application Ser. No. 10/762,583, filed Jan. 23, 2004, the entire contents of which are hereby incorporated by reference.

FIELD OF THE INVENTION

The present invention relates to a method for pulverizing physiological stones and removing scar tissues and for use in joint arthroscopy.

BACKGROUND OF THE INVENTION

TMJ syndrome, and related joint diseases, are manifested by the formation of relatively hard tissues entrapped in the synovial fluid adjacent to said joint. One mode of treatment is by the removal of the scar tissue located inside the TMJ. The scar tissue may be formed by acute trauma (e.g. a car accident) or chronic trauma (e.g. clenching or grinding), due to synovitis, or due to lack of mobility. Such a hard tissue in the temporomandibular joint usually results in a limitation of jaw opening. Treatment requires "passive motion" physical therapy, and surgery.

Joint arthroscopy, mostly in the knee but also in the shoulder, ankle and other small body joints, is one of the most common orthopedic surgical procedures. Arthroscopy is performed for a range of indications such as torn or damaged meniscus (menisectomy), chondramalacia (cartilage debridment), arthritis (synovectomy), torn or damaged ligament (tendon excision/resection) and other. Arthroscopy is performed as an out-patient procedure, usually under local anesthesia, by inserting an endoscope into the knee and insufflating the knee with saline to enable view and access to the different anatomical sites in the joint. Surgery is usually performed with powered mechanical tools such as shavers and burrs. Surgical tools are inserted into the patient's knee through small, 5 mm, incisions (ports). The limitations of these mechanical tools are their size (typically 4 mm diameter) which often blocks the view of a region of interest in the body, causes undesirable tissue removal and restricts access to tight joint spaces such as in the posterior horn.

Recently an RF technique (Coblation™, Arthrocare) has been introduced for arthroscopy. However, an instrument size (about 4 mm diameter), as well as surrounding necrosis, is still a limitation.

Attempts to introduce lasers to arthroscopy began about 20 years ago based on the potential of lasers to afford higher precision, no mechanical trauma and access to tight spaces due to thin delivery fibers. The first laser introduced in the late 80's was the $CO_2$ laser, delivered through hollow ceramic tubes. This laser was able to ablate all non-bony joint tissues with acceptable precision and surrounding necrosis. However, this laser could not be used with the regular saline insufflation of the joint, but required gas insufflation. While gas insufflation of the joint is technically possible, it entails a risk of gas emphysema and is not a standard technique. Therefore, the use of this laser in arthroscopy remained in the hands of very few arthroscopists. In the early 90's, a second attempt was made with the NdYAG laser in the contact mode. This technique was soon abandoned due to deep tissue necrosis and breakage of the fibers inside the knee.

The only laser type that was, in 90's, found applicable for arthroscopy (as well as discectomy) is Holmium laser. Later, in 1996, it was found that Holmium radiation based arthroscopy treatment might result in osteonecrosis. More specifically, a Holmium laser commonly used to repair knee joints has shown two contradicting effects: while being able to repair the knee in the short term, it caused hidden damage to surrounding cells and worsening the injury in the long term.

A recent advance in oral and maxillofacial surgery includes the delivery of laser energy through an arthroscope to the temporomandibular joint area in order to remove the hard tissue, which procedure replaces open joint surgery. Typical treatment includes administration of Holmium laser to the joint area. The procedure is carried out at an ambulatory care center, with discharge within several hours of the procedure. Most patients are back to work within 4-5 days. The conservative nature of laser debridement of adhesions is a significant aid in the treatment of the problems associated with TMJ dysfunction.

U.S. Pat. No. 5,582,190 to Slavin et al. teaches a Holmium-laser-based arthroscopic method for relieving symptoms caused by temporomandibular joint disorder in a patient. Their method is based on the following fourteen steps: (a) injecting a solution of lidocaine and epinephrine into a superior joint space of a temporomandibular joint of a patient, thereby providing distention thereof; (b) making a first vertical incision anterior to the posterior aspect of the tragus of the ear of the patient; (c) making a second vertical incision anterior to the first incision and below a line from the posterior aspect of the tragus of the ear to the lateral canthus of the orbit; (d) perforating the superior joint space bluntly with a first cannula and a first blunt trocar inserted into the first vertical incision and a second cannula and a second blunt trocar inserted into the second vertical incision; (e) advancing the first and the second cannula; (f) removing the first and the second trocar; (g) placing an arthroscope through the first vertical incision, allowing direct visualization of the joint; (h) placing a switching stick through the second vertical incision; removing the second cannula; (i) providing a dual-channel cannula having a distal end, a proximal end, a first and a second channel, each extending from the proximal to the distal end; (j) inserting the dual-channel cannula over the switching stick into an anterior recess of the superior compartment of the joint; (k) removing the switching stick; (l) locking the arthroscope into the first channel of the dual-channel cannula; (m) inserting an optical fiber into the second channel of the dual-channel cannula, the optical fiber for channeling radiation from a holmium laser; and (n) performing a desired surgical procedure within the joint space. According to Slavin's invention, the first and a second 2.0 mm cannula and a first and a second blunt trocar are used.

An additional example of removing hard tissues from relative soft organs is the pulverizing of physiological stones, and more particularly, the removal of calcium stones from the salivary ducts. The mechanism of salivary stone formation is unclear, but seems to be multi-factorial. About 1% of people suffer from salivary stones. Most stones form in the submandibular gland (85%) and the remainder in the parotid (15%).

The elimination of stones from the body, such as kidney stones and gallstones has been known for decades. Lithotripsy is the pulverization and removal of urinary or other calculi using a lithotripter. A lithotripter is capable of fragmenting kidney stones with ultrasound waves. The majority of patients (85-90%) are rendered symptom free and in 30-50% of cases, the stones are completely cleared from the salivary glands. The remainder retains some stone debris.

There has been an increased interest in pulsed erbium lasers operating in the 3-μm region for tissue ablation. These lasers advantageously emit wavelengths very highly absorbable by tissue water, thus would cause minimal damage to surrounding tissues.

The range of clinical applications for these lasers is continually expanding due to the controllable qualities of cutting, removal and pulverization of soft and hard tissues, which make these wavelengths attractive for minimally invasive surgical treatments. However, as most clinical treatments in orthopedics, angioplasty, ophthalmology, or lithotripsy, are performed in a liquid environment, often in a non-contact mode, most of the laser energy is absorbed in the water and little is left for tissue ablation.

Erbium is a metallic element of the rare-earth group. Erbium is always found in combination with yttrium, another rare earth, and the ore is mined in the form of yttrium-aluminum-garnet (YAG).

The Erbium YAG laser emits a 2940 nm wavelength beam of light. Due to the extremely strong absorption of its 3 μm-radiation in biological tissue, the erbium laser has become a very useful and precise tool in surgery. The resulting penetration depths are around 2-3 μm and thus offer a minimal invasive and precise ablation of tissue.

Holmium lasers have an advantage when transmission of the laser beam over longer distances is required, such as when transmitting the energy from the apparatus to the kidneys, while Erbium lasers are effective for shorter distances as their energy can not be transmitted through conventional silica fibers.

Erbium laser frequencies are highly effective for the treatment of hard tissues, because of the ability to pulverize these hard tissues. Consequently, Erbium YAG lasers are used in dentistry as substitute for the painful, noisy drill, especially for clearing the areas of tooth decay.

The use of Erbium lasers for laser lithotripsy of salivary stones is unknown in the art. The idea of using Erbium lasers for endoscopic lithotripsy was initiated in 2001, but not for the salivary glands. Erbium lasers have been researched for urology for the removal of kidney stones (Chang et al., *Journal of Urology*, 168:436-441, (2002)), and are well known for drilling of teeth.

U.S. Pat. No. 6,375,651 to Grasso III et al. discloses a medical device, which requires a suction conduit, and an energy-transmitting conduit wherein at least some of the transmitted energy is directed to the distal region of the suction conduit. The said device includes an optical apparatus for directing the energy. The device has applications in lithotripsy and tissue-removal in a patient. Ho:YAG laser was claimed to be useful for such procedures. The inventors also suggested to utilize lasers based on thulium (Th), Erbium: yttrium-aluminum-garnet (Er:YAG) (190 to 350 μm), HF, DF, CO, and $CO_2$ in the mid-infrared region, and excimer lasers in the ultraviolet region. However the technology disclosed in this publication is unsuitable for pulverizing stones in the salivary ducts because suction is not possible in physiological conduits as small as the salivary ducts, which have a maximal diameter of 3 mm.

It is well acknowledged that introduction of a suction means in the manner defined in this patent will promptly and irreversibly collapse the fragile salivary duct and this is probably the reason why the treatment of such small-diameter ducts is not defined specifically as embodiments of this patent.

U.S. Pat. No. 6,395,000 to Mitchell et al. discloses a medical laser system for ablating biological material. The system also includes an Er:YAG laser useful for various ophthalmic procedures, including capsulotomies, sclerostomies, excision of pupillary membranes, cutting of vitreous bands and iris margin. The system is described by the inventors to be also useful for a variety of urinary organ procedures such as kidney wall modification, stone (calculi) fragmentation and removal in the kidney, gall bladder and ureter (lithotripsy), transurethral incision of the prostate, prostatectomy, ureter lesion removal, vasal tissue removal, nephrectomy, vasovasotomy and lymph node modification. Moreover, the system supposed also to be useful for opening strictures in the aorta, modifying vessels at an aneurysm, for clearing vessels (angioplasty) and for removing clots. However, the system as described in aforementioned Mitchell's patent was not found useful for pulverizing stones in the salivary gland ducts.

SUMMARY OF THE INVENTION

The present invention relates to a novel method for delivering Erbium laser light to a treatment target located inside a fluid-filled body cavity, as well as a method for joint arthroscopy by high-intensity pulsed light of about 2700-3000 nm (e.g., Erbium laser light).

Thus, according to one broad aspect of the invention, there is provided a method for use in joint arthroscopy, the method comprising: producing a beam of pulsed laser radiation of a wavelength range of about 2700-3000 nm and a predetermined frequency of pulses; directing said pulsed beam to a joint region inside a fluid medium and maintaining it substantially focused on a treatment target within the joint region during a predetermined time period, thereby effecting tissue within said treatment target by said laser radiation.

According to another broad aspect of the invention, there is provided a method for carrying out arthroscopy of damaged meniscus, the method comprising: producing a beam of pulsed laser radiation of a wavelength range of about 2700-3000 nm and a predetermined frequency of pulses; directing said pulsed beam to the meniscus inside a fluid medium and maintaining it substantially focused on the meniscus during a predetermined time period.

According to yet another broad aspect of the invention, there is provided a method for delivering Erbium high-intensity laser light to a target inside a fluid filled body cavity, the method comprising: passing the laser light though a hollow wave-guide made of a material substantially reflective to wavelengths of about 2700-3000 nm, and being sealed at its distal end, by which it is brought to the cavity, by a tip portion made of a material substantially transparent to said wavelengths; and inserting said distal end into the fluid-filled cavity to irradiate the vicinity of the target by the laser light.

Examples for the target concerned are tissues or calcifications in the temporomandibular joint, the knee, shoulder, ankle or any other body joint. Another example for a treatment zone is a tissue or calcification in the salivary glands. The method is to be used for example when the tissue is a fibrous scar tissue, a torn or damaged meniscus or calcified tendons, thus being subject to medical treatment.

The laser light energy properties (intensity, and/or wavelength, and/or pulse frequency, duty cycle, etc.) could be adjusted for incising a hard tissue, ablating it or disintegrating it to fragments.

The invented method preferably also utilizes imaging of the target (e.g., joint region). This may be implemented using an endoscope. The endoscope may be a stand alone device, or the endoscope and the hollow waveguide may be connected to the common hand piece.

In a typical adjustment the surgeon determines the intensity parameter of the laser beam in the range between 200-2000 millijoule, e.g., about 500-1500 millijoule.

According to yet another broad aspect of the invention, there is provided a probe comprising a hollow wave-guide made of a material substantially reflective to wavelengths of about 2700-3000 nm, and being sealed at its distal end, by which it is brought to the body, by a tip portion made of a material substantially transparent to said wavelengths.

The present invention is based on the use of Erbium laser radiation (e.g. Erbium yttrium-aluminum-garnet (Er:YAG) laser) for various types of treatment, such as treating hard tissues entrapped in a cavity comprising body fluids, wherein said cavity diameter is less than 3 mm, and also in joint arthroscopy dealing with larger cavities. This is surprising in view of the fact that typically for small cavities (about 3 mm) heating of the cavity and the fluid in it is a major problem that may cause substantial damage to the tissue. This problem of heating is of no concern in the typical uses of Erbium laser in treating hard tissue present in large cavities such as kidneys (Chang et al. Supra) as in such large cavities the bulk of the tissue and liquid may absorb part of the heat. This finding is also contrary to the typical use of holmium lasers for removal of stones from small cavities and further more it was found by the inventors of the present invention that holmium laser does not give satisfactory results as the stone is disintegrated to fragments that are too large for convenient flushing.

Thus, the present invention for example concerns a method for the treatment of hard tissues present in a fluid-filled body cavity, the cavity having a diameter of 3 mm or less, the method comprising: applying to, said hard tissue or to the vicinity of said hard tissue a laser beam produced by Erbium laser device.

The term "fluid-filled body cavity" refers both to a fluid filled lumen of a physiologic conduit such as salivary glands, as well as to small fluid filled cavities such as those present in the temporomandibular joint or other body joints such as the knee, the shoulder or the ankle.

The term "in the vicinity"—means from contact and up to 1-2 mm away from the stone or the tissue to be treated, at which distance the energy can still reach the stone (or the tissue) due to the "bubble" effect.

The method of the invention is achieved by applying either directly to the hard tissue, or to the fluid present in the vicinity of said hard tissue, preferably at a distance of up to 1-2 mm the laser beam so that its focus is either at or at said vicinity to the treated hard tissue. Typically, in accordance with the present invention, the energy parameters of the laser beam are between 200-1000 millijoules, preferably 300-700 millijoules, most preferably 300-500 millijoules, when treating small cavities such as of the salivary glands. When treating lager cavities such as when treating the knee, the energy parameters may be between 200-2000 millijoules, and more commonly between 300-1500 millijoules. Spot size of the beam on tissue is typically in the range of 0.3-1.5 mm but preferably 0.5-1.0 mm.

The beam is produced by an Erbium laser device. As will be shown in the example, the use of Erbium laser has the beneficial effect that the fragments of the calculi produced, have a very small diameter, and thus can be easily flushed out from the cavity, even if its diameter is 3 mm and less.

Preferably, in accordance with the present invention, the laser device is located inside an endoscope.

By another aspect, the present invention concerns a system for treatment of hard tissue present in a fluid-filled body cavity, the cavity may have a diameter of 3 mm or less, the system comprising an endoscope for visualizing the interior of the treated cavity, and a device for the production of an Erbium laser beam. Preferably, the device is in fact a hollow endoscope through which the laser beam is administered.

The laser beam preferably is adapted to generate the beam having the energy parameters of between 200-2000 millijoules.

Typical treatment time can be determined empirically on a case by case basis as the disintegration of the hard tissue is typically continuously monitored by an endoscope. Typical treatment times are about 1 to 15 minutes.

In accordance with the invention the fluid-filled body cavities may be ducts of the salivary glands and the hard tissue may be calculi, or salivary stone.

According to one particular embodiment the endoscope is a Nahlieli type sialoendoscope, and the delivery of said laser beam is provided by a curved optical fiber.

The method of the present invention may be used for the disintegration and subsequent removal of calculi and in particular for disintegration and removal of salivary stones.

By another option the present invention may be used for relieving symptoms caused by scars and other temporomandibular joint disorders in a patient, even in cases where the fluid-filled joint (being the fluid-filled cavity) has a diameter of less than 3 mm. As in the case of calculi, also for the treatment of scar tissue, the laser beam is directed to said scars at close proximity so as to disintegrate the hard tissue. Said Erbium laser is effective in the pulverization of said scars, to fragments having a diameter of less than 2 mm. Specifically, the scars are selected from hard tissues caused due to diseases or disorders of the TMJ and its surrounding regions.

The method of the invention is typically carried out by the following steps: (a) providing an endoscope for visualizing the interior of the body-filled cavity such as salivary glands; (b) providing an Erbium laser device to generate a laser beam in order to pulverize the hard tissue (such as salivary stones, joint scars, etc.); (c) applying a laser beam produced by the device through said endoscope to the hard tissue to be treated or to its vicinity. The laser beam is directed at said hard tissue (such as salivary stones, joint scars etc.) or at close enough proximity to the stones so that said Erbium laser is capable of pulverization of said stones in the way calculi fragments having a diameter less than 2 mm are produced.

More specifically, the endoscope is a Nahlieli type sialoendoscope. Preferably the delivery system of said laser beam is by a curved optical fiber. Typically the laser beam is transferred from the Erbium device (which may be for example a conventional device used in dentistry), by a fiber for transmittal of laser beams which may be germanium oxide glass, sapphire or a hollow waveguide.

Typically the length of the fiber incorporated in the endoscope is 10-25 cm.

BRIEF DESCRIPTION OF THE DRAWINGS

In order to understand the invention and to see how it may be carried out in practice, some preferred embodiments will now be described, by way of non-limiting examples only, with reference to the accompanying drawings, in which.

DETAILED DESCRIPTION OF THE INVENTION

As set forth above, it is one of the aspects of the present invention to treat hard tissues entrapped in a cavity comprising body fluids, wherein said cavity has a diameter of less than 3 mm so treatment of the hard tissue is achieved without causing a substantial heating of the fluid and the small sized fluid filled cavity. Such a heating presents a major problem and prior the present invention prevented effective and safe treatment of hard tissues in such small cavities.

Prior to the present invention there was no satisfactory solution for the treatment of hard tissue entrapped in small, fluid-filled cavities, and there was no way to provide a treatment that would enable on the one hand, to disintegrate the hard tissue to small enough fragments to be easily flushed out, and on the other hand, to do so without substantial (i.e. tissue damaging) temperature increase in the fluid-filled small cavity.

Two examples are hereto provided, wherein the first is the treating of scars and other diseases and disorders in the temporomandibular joint (TMJ). The second is treating of calcium stones, especially those located in the mandibular salivary ducts. Those two examples and the following description which is provided below, along all chapters of the present invention, are described to enable any person skilled in the art to make use of said invention and set forth the best modes contemplated by the inventor of carrying out this invention.

Various modifications, however, will remain apparent to those skilled in the art, since the generic principles of the present invention have been defined specifically to provide the erbium yttrium-aluminum-garnet (Er:YAG) laser system.

Figure 1:
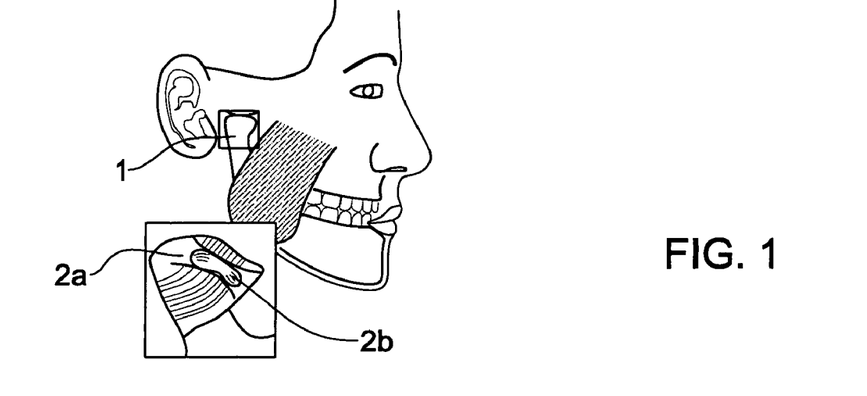
FIG. 1 is a schematic illustration of the temporomandibular joint and a magnified view thereof.

Reference is made now to FIG. 1 describing the TMJ 1 located in the joint of the mandibular and maxillary bones. A magnified presentation of said TMJ is presented to comprise of a connective tissue (2*a*) and a disc 2(*b*).

Figure 2:
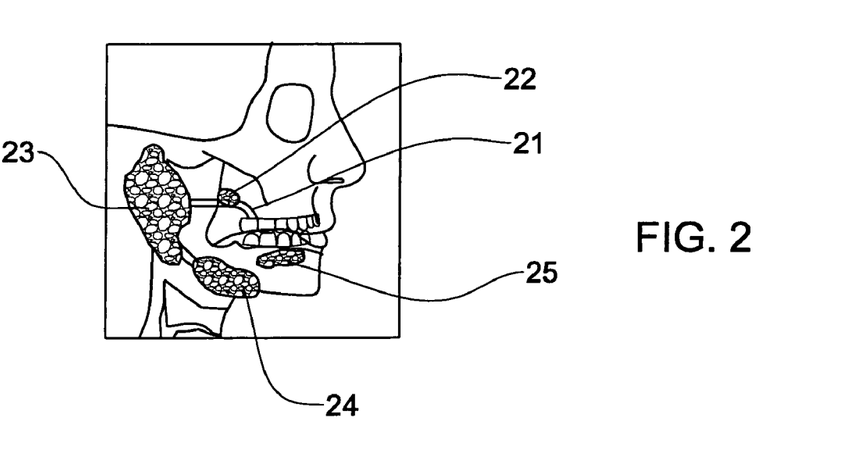
FIG. 2 is a schematic illustration of the salivary glands and ducts where salivary stones may develop.

Reference is made now to FIG. 2, schematically presenting the salivary glands: parotid duct 21 communicating the mouth with the accessory parotid gland 22 the parotid gland 23 and the submandibular gland 24 and the sublingual gland 25.

For endoscopic laser lithotripsy of salivary stones, it is determined that 85% of salivary stones are located in the sub-mandibular gland 24 and 15% in the parotid 22, 23 glands. This is the area of the mouth and jaws. Most stones are composed of calcium phosphate. Typical size range is 5-20 mm. Complete fragmentation requires fragments less than 2 mm, so that they can be effectively disintegrated.

Figure 3A:
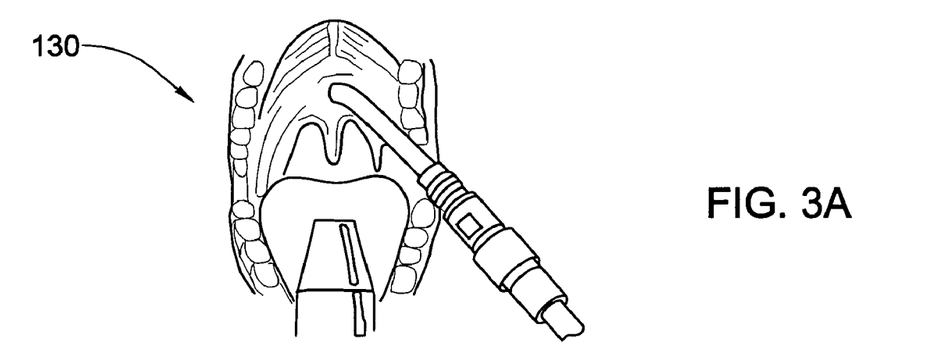
FIG. 3A shows a manner of treatment of salivary stones.

FIG. 3A shows the laser applied to the salivary glands of a patient 130, and delivered through the mouth cavity.

Figure 3B:
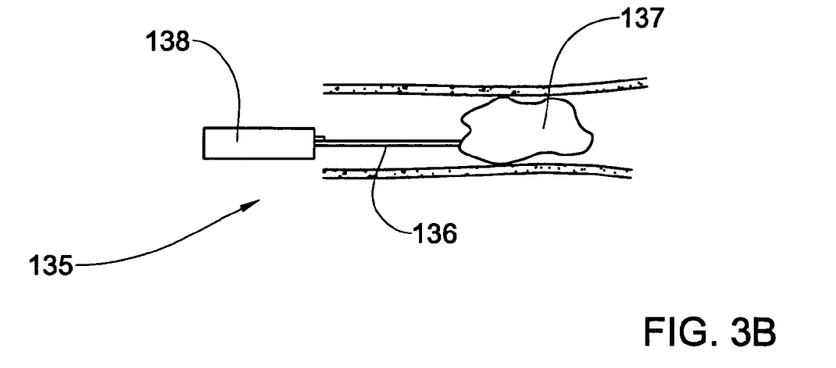
FIG. 3B shows the positioning of the laser-emitting fiber in a salivary duct for the treatment of stones.

FIG. 3B shows reference block diagram 135 of the placement of the endoscope and the optic fiber in salivary ducts, wherein 137 is the stone, 138 is the endoscope and 136 the laser fiber.

Figure 4A:
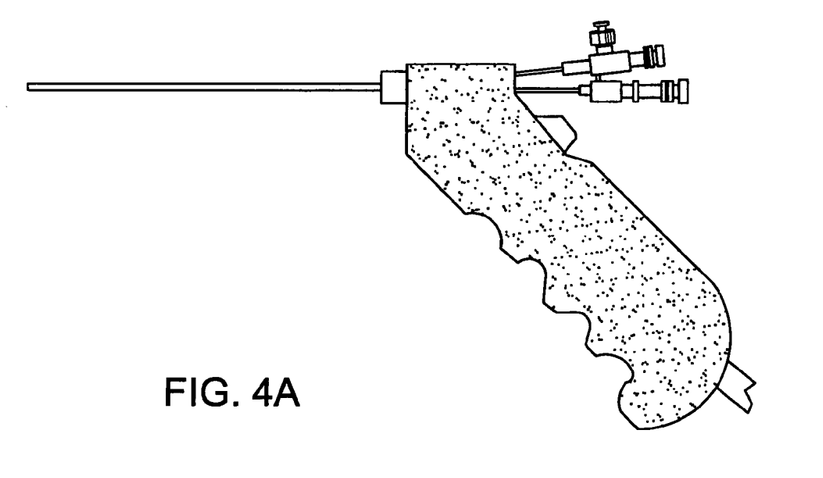
FIG. 4A and FIG. 4B is a schematic illustration of two types of Nahlieli sialoendoscopes.
Figure 4B:
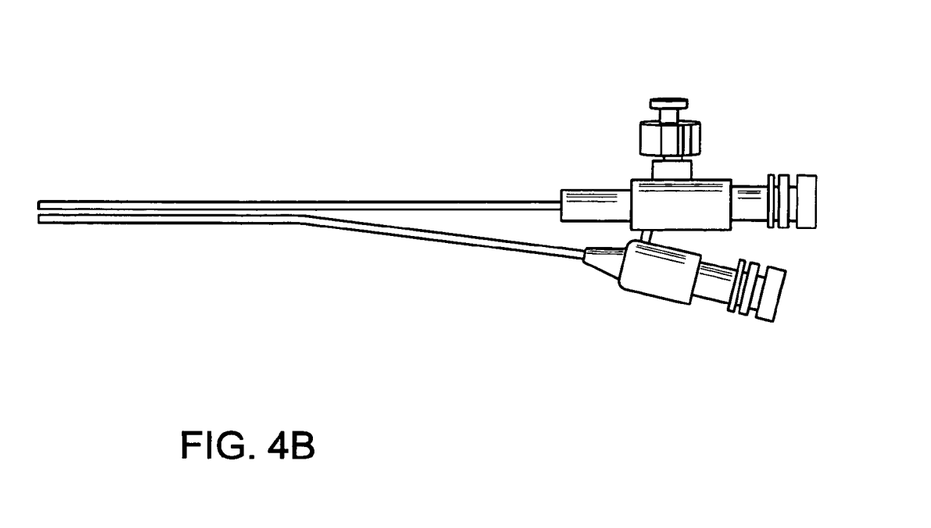

The endoscopes used such as in FIGS. 4A and 4B may be a Nahlieli type sialoendoscope, and delivery of said laser beam is by a curved optical fiber. The Nahlieli sialoendoscope, as such as the device Type 1 or 2 commercially available by Karl Storz Ltd. This is an endoscope useful for the diagnosis and treatment of inflammatory salivary gland diseases and for minimal temporo-mandibular-joint arthroscopy (denoted in the present invention in the term 'Nahlieli type sialoendoscope'). The hereto-defined Storz's Nahlieli sialoendoscope usually comprising two separate channels, with two blunt obturators and two LUER-lock adapters, curved channel for instruments up to 3 Fr., O.D. 1.3 mm, straight channel for use with the commercially available Miniature Telescope 28620 with lateral LUER-lock adapter for irrigation, O.D. 1.3 mm, working length 4 cm, overall length 10.7 cm.

Reference is made now to FIG. 4A, presenting a side view of a Karl Storz commercially available Nahlieli sialoendoscope, comprising a handle and blunt obturator, for use with a miniature telescope diameter 2.3 mm×1.3 mm, working length 12 cm, and an operating sheath with obturator valve. Similarly, FIG. 4B is presenting a side view of another commercially available Nahlieli sialoendoscope comprising with two separate channels, with two blunt obturators and two LUER-lock adaptors, curved channel for instruments up to 3 Fr., O.D. 1.3 mm, straight channel for use with miniature telescope with lateral LUER-lock adaptor for irrigation, O.D. 1.3 mm, working length 4 cm, overall length 10.7 cm.

It is in the scope of the present invention, wherein the laser is an ErbiumYAG laser.

Figure 5:
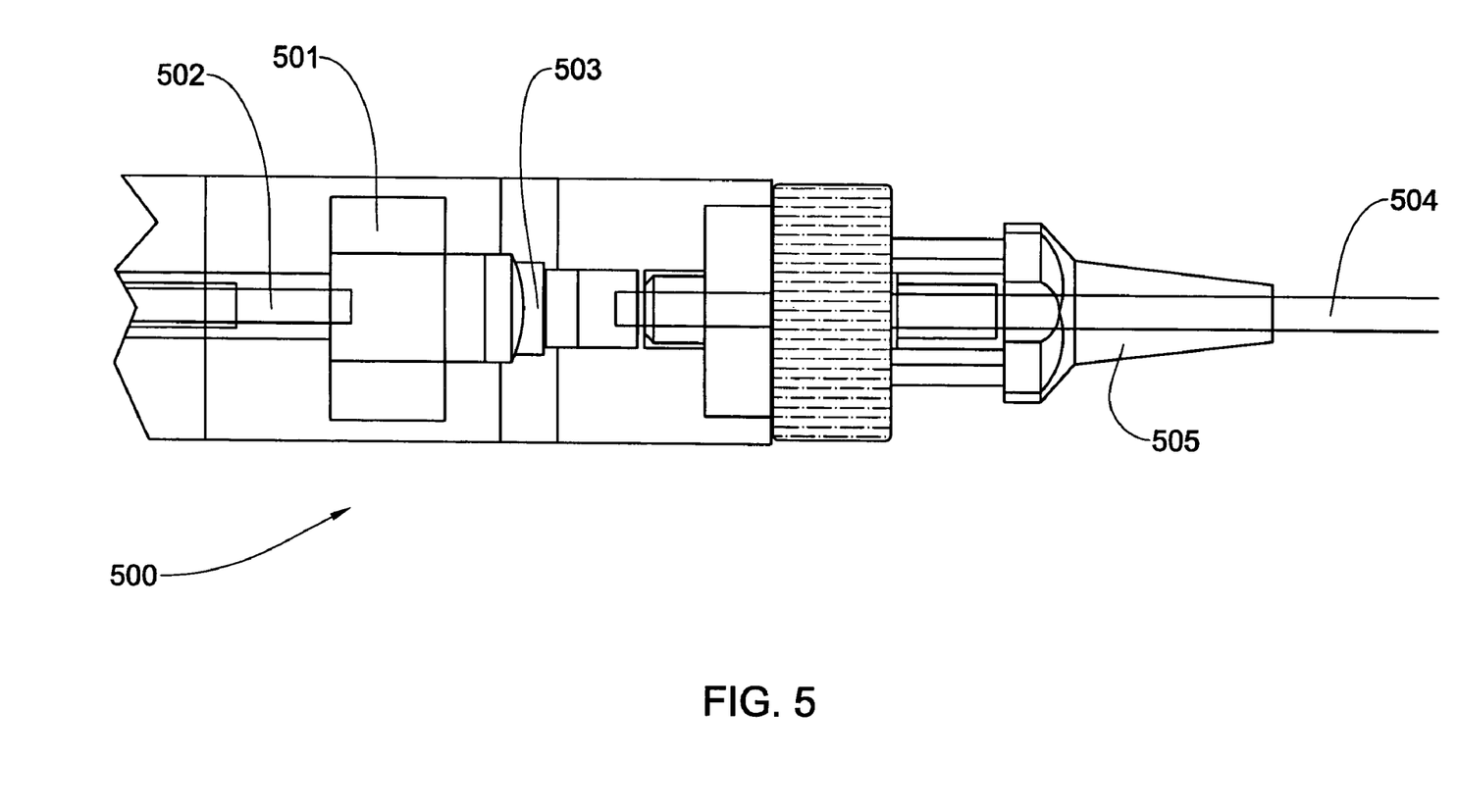
FIG. 5 is a schematic illustration of an add-on apparatus for attachment into a standard Er:YAG laser device.

Reference is now made to FIG. 5 which shows an apparatus 500 which is part of a system for carrying out the invention. This apparatus is a focusing hand piece which attaches, at its proximal end 501 to a dental Erbium laser delivery fiber 502. The hand piece houses focusing lenses (e.g. ZnSe lenses) 503 to focus the beam emitted from the laser fiber into the endoscopic fiber 504. The endoscopic fiber 504 is attached at the distal end of the hand piece through a quick connect mechanism 505 such as an SMA connector. The endoscopic fiber 504 is inserted into the operating channel of the Nachlieli endoscope (for example as shown in FIG. 4A or 4B). A luer lock (not shown) may be incorporated over the SMA connector to firmly secure the fiber and the hand piece to the endoscope so that the surgeon may hold the entire device in one hand.

Figure 6:
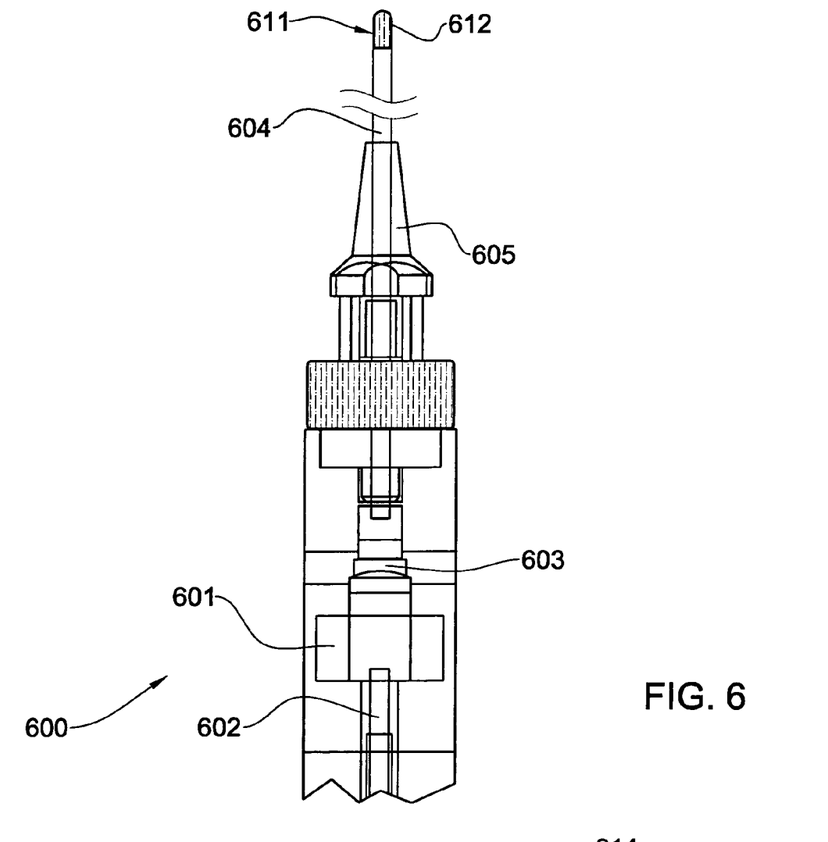
FIG. 6 illustrates a device of the present invention suitable for joint arthroscopy; as well as for other treatment of tissues in small bodily cavities.
Figure 7A:
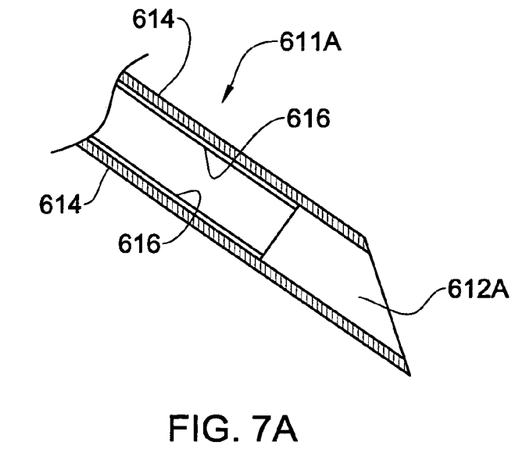
FIGS. 7A and 7B illustrate two example of a probe device of the invention suitable to be used in the device of FIG. 6.
Figure 7B:
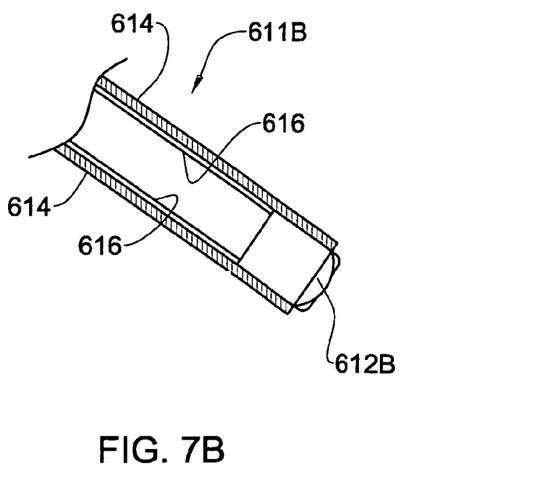

FIG. 6 illustrates an apparatus, generally at 600, of the present invention configured and operable for use in arthroscopy. The apparatus 600 is configured generally similar to the above-described apparatus 500, namely presents a focusing hand piece having its proximal end 601 coupled to an Erbium laser delivery fiber 602, and includes focusing lenses 603 for focusing the Erbium beam into an endoscopic fiber 604. The latter is preferably an integral part of the entire device 600. In the device 600, the endoscopic fiber 604 is configured according to the invention for effectively delivering Erbium radiation towards a target while in the fluid-filled bodily cavity. To this end, distal end 611 of the hollow wave guide 604 is sealed by a sapphire tip 612. The sapphire tip 612 is preferably mounted on the wave guide pipe 611 such that a small part of the tip 612 projects out of the pipe 611 or such that the tip 612 is entirely concealed inside the hollow wave guide 611. This is shown in the examples of FIGS. 7A and 7B. It should be understood that the smaller the projecting part the less damage (affecting optical properties of the tip) to the sapphire body 612 that might be caused by hits of ablated calculi particles.

FIGS. 7A and 7B also show that the distal end of the waveguide 604 may be wedged or substantially planar or arced. As further better seen in FIGS. 7A and 7B, the waveguide 604 is made of a hollow pipe 614 made of a material reflective to wavelength radiation of 2700-3000 nm (preferably metal pipe which may or may not be coated by another material external coating), and its inner surface is coated with a dielectric material layer (film) 616.

EXAMPLE 1

The Use of an Erbium Laser for Lithotripsy of Salivary Stones

A. Set up:

Erbium laser used for the tests was a commercial OpusDuo dental laser produced by Lumenis Ltd., Israel. This laser is a free-running, 2.94 µm laser which emits 250 µsec pulses at a maximum rate of 20 Hz. Energy per pulse can be adjusted from 100 mJ to 1000 mJ. Maximum average power is 20 Watt.

The laser beam is delivered through a flexible, metal, hollow fiber to a handpiece which may be detached. Beam spot size at the handpiece output aperture is 1 mm.

Some of the tests were conducted using the standard system handpiece fitted with short sapphire tips (straight or tapered) to deliver the energy to the stones while some of the tests were conducted using various commercially available infrared fibers such as sapphire fibers (Photran Inc., U.S.A.), hollow glass fibers (Polymicro, U.S.A.) or germanium oxide glass fibers (Infrared Fiber Systems, U.S.A.).

1 mm. core fibers were "butt" coupled to the system handpiece while smaller diameter fibers were connected using ZnSe lenses to focus the laser beam into the fiber.

Fiber diameters were 1 mm. or 0.75 mm, core.

B. Test Results:

In vitro lithotripsy of human, extracted, salivary stones was conducted both in air and in water to test optimal fragmentation parameters. In air, 200 mj with a spot of 1 mm and a frequency of 20 Hz resulted in efficient fragmentation to dust-like particles. Energy increase to 300 mj appeared clinically to be too aggressive with substantially larger fragments. In all cases fragmentation was conducted in contact or close contact to the stone. While fragmentation was found to be clinically efficient, lithotripsy in an air environment resulted in rapid contamination of the fiber output surface by stone debris which caused fiber damage. Even small salivary stones could not be fragmented before onset of this catastrophic damage mechanism. Contamination persisted even with a fiber-stone distance of 3-4 mms. though efficiency decrease due to beam divergence out of the fiber. Additionally large fiber-stone distances are endoscopically not practical.

To overcome this problem, fragmentation was conducted in a water filled container with the fiber tip in contact with the stone. It was found that in a water environment fiber tip durability is increased even though laser energies have to be increased to obtain clinically efficient fragmentation rates. Using a 1 mm spot size, threshold for clinically efficient fragmentation was found to be 300 mJ per pulse, while optimal range was 500-700 mJ per pulse. Optimal pulse rates were 15-20 Hz. Stone fragmented to microscopic, dust-like particles which floated in the water, with occasional larger fragments (2-3 mm) which broke off particularly from softer stones.

The surface of a 1 mm. sapphire tip, in contact with the stone under water, did not exhibit any damage or degradation at all energy levels up to 1000 mJ, the maximum energy available from the laser.

Use of the smaller fiber diameter resulted in more efficient fragmentation due to the higher energy densities, but resulted in fiber tip damage with some of the fibers used.

EXAMPLE 2

Comparative Results—Er:YAG Laser to Holmium Laser

The comparison was perform between Er:YAG laser and Holmium laser the latter being the standard laser used for lithotripsy in urology.

Comparison was carried out in vitro, testing the size and nature of fragmentation of extracted, human salivary stones placed in a water filled metal container which was to simulate a small cavity filled with liquid. Delivery of the Holmium laser was through standard, commercial low-OH silica fibers.

Test confirmed literature report that fragmentation efficiency of Erbium is roughly twice that of Holmium.

Fragmentation rate of Erbium at 10 Hz, 0.5 J/pulse was similar to that of Holmium at 10 Hz, 1 J. These are the conventional Holmium parameters used in clinical work. Additionally test showed that stone fragments following Erbium lithotripsy are smaller than with Holmium.

This was visually observed by the fact that for the same stones, most Holmium fragments immediately sunk and accumulated at the bottom of the container while with the Erbium, fragments floated in the water as a "cloudy" suspension.

These results indicate that the method of the invention is more effective in disintegrating stones, in particular salivary stones, than treatment with Holmium laser or other pulverization means.

Having described the invention with regard to certain specific embodiments thereof, it is to be understood that the description is not meant as a limitation, since further modifications will now suggest themselves to those skilled in the art, and it is intended to cover such modifications as fall within the scope of the appended claims.

EXAMPLE 3

Knee Arthroscopy

This example demonstrates the experimental results of using the device 600 (FIG. 6) of the present invention in a clinical procedure applied to a porcine knee (device used employed a substantially flat-shaped sapphire tip slightly protruding out of the metal tube). Erbium laser radiation used was a commercial OpusDuo dental laser commercially available from Lumenis Ltd., Israel. The test procedure has been performed when the porcine knee being irrigated by saline solution. The laser beam was delivered from the laser source (Erbium laser) to the target (i.e., the meniscus of the porcine knee) through the waveguide 604 (which may be detachable). The operational mode was such that the beam spot size at the handpiece aperture (i.e., at that entrance of the lens arrangement 603) was 1 mm. The fiber probe 604 was a 14 cm in length and with an inner diameter of about 0.6 mm). The distal end of the probe was placed in contact or very near contact to the meniscus tissue.

Generally, the treatment of the kind specified can be carried out with the laser pulsed radiation energy in a range of 200-2000 millijoule. In the present experiment, the Erbium source operated in a pulse mode generating 300 mj pulses at a frequency of 20 Hz, and during the device operation the meniscus of the porcine knee was incised in several tens of seconds.

Generally, the inventors have found that a treatment time may be from about ten seconds to a few minutes.

The invention claimed is:

1. A method for treating a target tissue within a body cavity filled with a fluid medium and comprising a joint, the method comprising:

producing a beam of pulsed laser radiation of a wavelength range of about 2700-3000 nm and a predetermined frequency of pulses;

directing said pulsed beam to a region of said joint within said fluid medium and maintaining said beam substantially focused on a treatment target within said joint region during a predetermined time period, thereby treating tissue within said treatment target by said laser radiation; and wherein said directing of said pulsed beam includes:

providing a hollow wave-guide pipe made of a material reflective to said wavelength range, having a dielectric inner surface, and being sealed at a distal end thereof by a sapphire tip-like portion; and placing the distal end of the pipe in contact or very near contact to the treatment target.

2. The method according to claim 1, wherein said sapphire tip-like portion is located inside the pipe substantially not protruding therefrom.

3. The method according to claim 1, wherein said sapphire tip-like portion is located inside the pipe slightly protruding therefrom.

4. The method according to claim 1, wherein the region of said joint includes at least one of the following: a tissue or calcification in the temporomandibular joint, the knee, shoulder, ankle, fibrous scar tissue, torn, damaged meniscus, and calcified tendons.

5. The method according to claim 1, further comprising endoscopic imaging of the joint region.

6. The method according to claim 1, wherein the intensity of the laser beam is about 200-2000 millijoule.

7. The method according to claim 6 wherein the intensity parameters of the laser beam is about 500-1500 millijoule.

8. A method for delivering Erbium high-intensity laser light to a target inside a fluid filled bodily cavity comprising a joint, the method comprising: passing the laser light though a hollow wave-guide made of a material substantially reflective to wavelengths of about 2700-3000 nm, and being sealed at its distal end, by which it is brought to the cavity, by a tip portion made of a material substantially transparent to said wavelengths; and inserting said distal end into the fluid-filled cavity to irradiate the vicinity of the target by the laser light.

* * * * *